United States Patent [19]
Sneider

[11] 3,993,070
[45] Nov. 23, 1976

[54] EXPANDABLE SYRINGE

[76] Inventor: Vincent R. Sneider, 3422 Hallcrest Drive, Atlanta, Ga. 30319

[22] Filed: June 30, 1975

[21] Appl. No.: 591,612

[52] U.S. Cl. ................................. 128/251; 128/232
[51] Int. Cl.² ......................................... A61M 7/02
[58] Field of Search .......... 128/232, 230, 251, 224, 128/239, 247, 227; 215/11

[56] References Cited
UNITED STATES PATENTS

| | | | |
|---|---|---|---|
| 2,782,784 | 2/1957 | Ritter | 128/232 |
| 3,401,695 | 9/1968 | Rosenberg et al. | 128/232 |
| 3,773,047 | 11/1973 | Sneider | 128/232 |

*Primary Examiner*—John D. Yasko
*Attorney, Agent, or Firm*—Jones, Thomas & Askew

[57] ABSTRACT

An expandable syringe having a pressure sensitive valved filling means at one end for admitting the liquid under pressure to fill the syringe, and an opening at the opposite end having a valved dispensing means fitted therein, the dispensing means being adapted to receive a cap having a nozzle mounted thereon.

5 Claims, 7 Drawing Figures

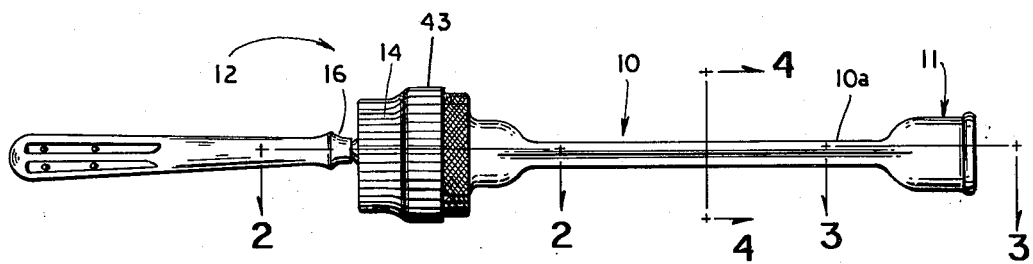
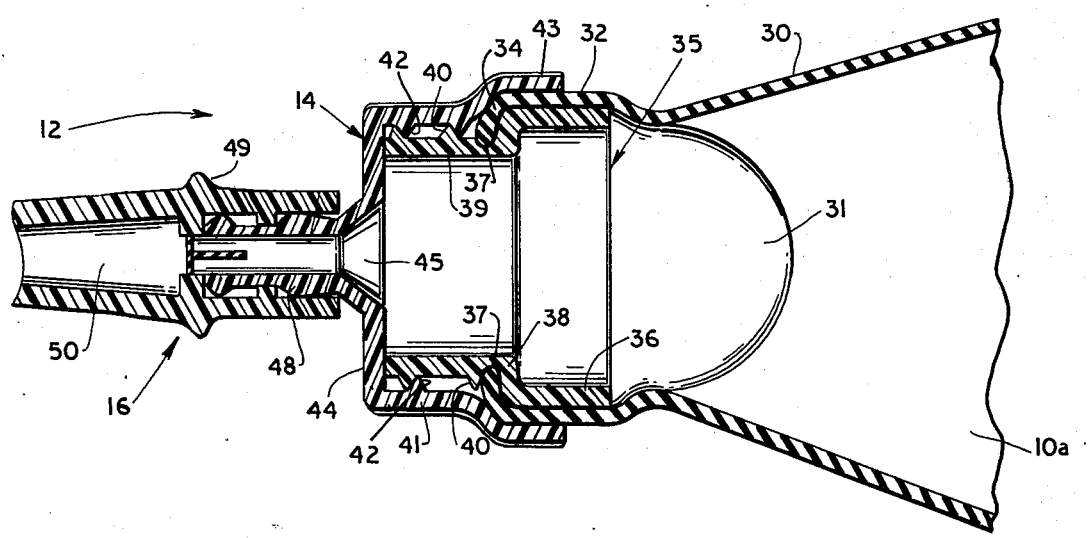
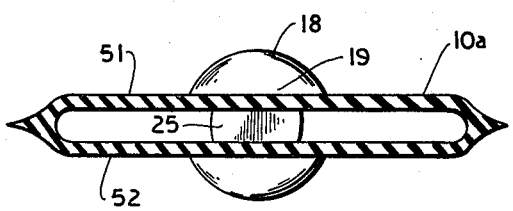
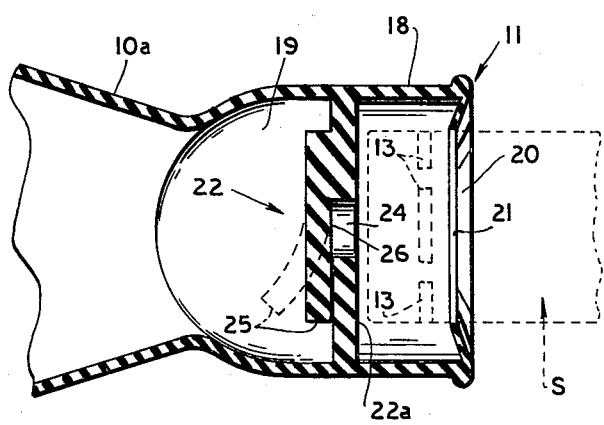
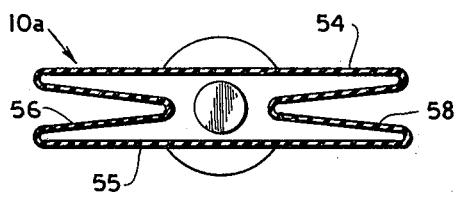

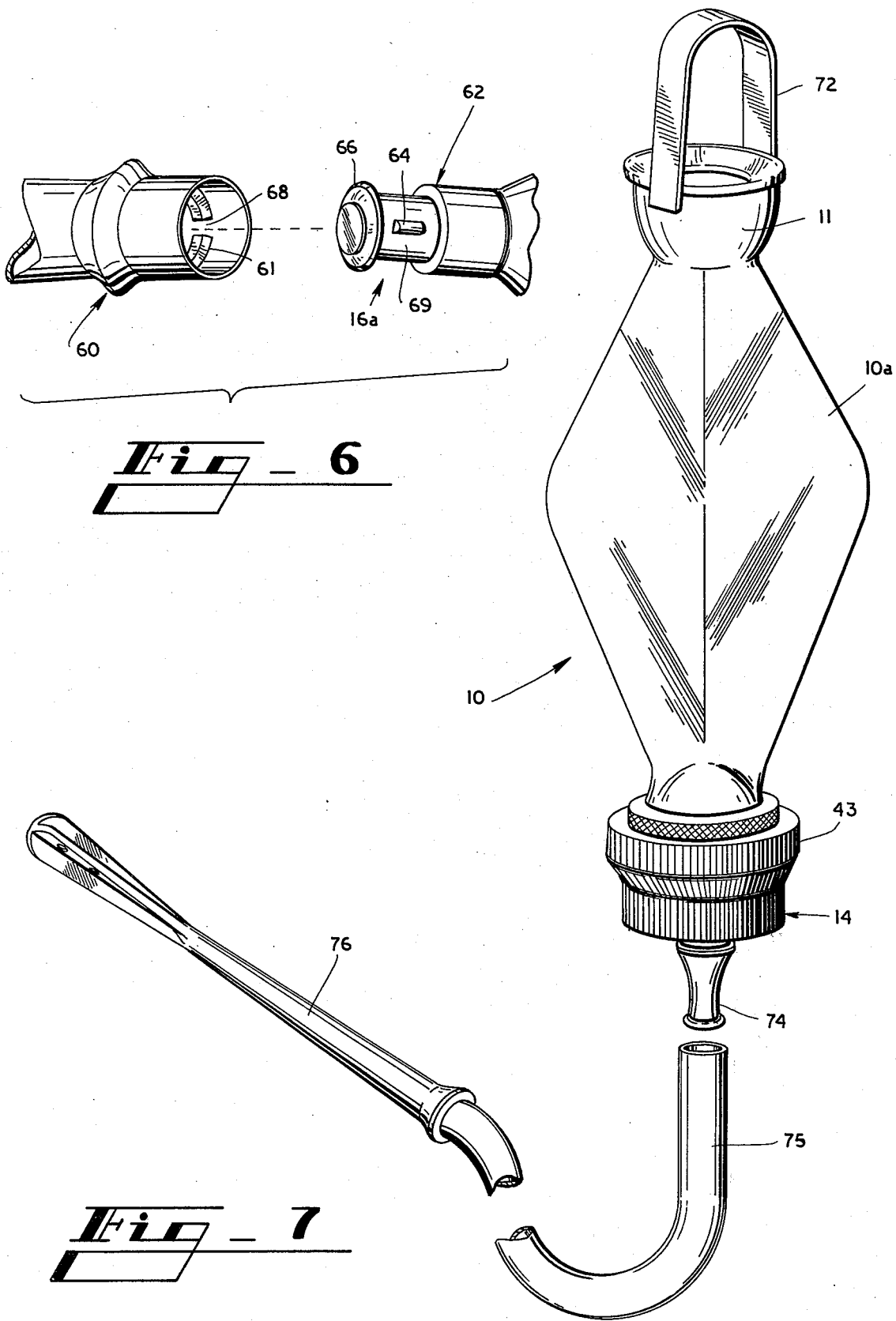

EXPANDABLE SYRINGE

This invention relates to an expandable syringe, and is more particularly concerned with a reusable syringe for providing vaginal douches, enemas and the like.

Vaginal douche devices, and particularly vaginal syringes are well known in the art and in commerce. One general form of syringe includes a substantially flat bag which may be expanded by filling with water or other appropriate liquid. After the liquid has been placed in the bag, a nozzle is inserted into the filling spout of the bag so that the apparatus may be used as a syringe. The expanded bag may be depressed to assist in urging the liquid from the bag, and through the nozzle. One particular syringe of this general description is known as the "Shy" douche device.

While syringes of the above described general type have been used for some considerable length of time and have achieved some commercial success, there are several problems inherent in the design of this type of prior art syringes. Generally, once the nozzle is inserted into the syringe, there is no means for controlling the flow of liquid from the syringe and through the nozzle. When there is pressure because of the introduction of a quantity of liquid under pressure into the syringe, it is possible to inadvertently dispense the liquid upon insertion of the nozzle into the syringe. Also, since the filling spout includes a valve which is openable by either water pressure of the insertion of a nozzle, it is virtually impossible to empty the syringe after usage thereof, and it is equally difficult to rinse any chemicals out of the syringe before the syringe is stored.

The present invention overcomes the above-mentioned and other difficulties by providing an expandable syringe having filling means at one end thereof, and dispensing means at the other end thereof. With the syringe of the present invention, it will be understood that the syringe may be filled in conventional fashion, the filling means including a valve for closing the filling spout when the syringe is filled. The dispensing means includes a valve which may be closed during filling of the syringe. There is no danger of inadvertent dispensing of the liquid from the syringe until the syringe is ready for use because the liquid is confined within the syringe by the valves. The dispensing means includes a removable cap so that the syringe may be emptied following use and the syringe may be rinsed with water to remove any traces of chemical residue therefrom. These and other objects, features and advantages of the present invention will become apparent from consideration of the following specification, when taken in conjunction with the accompanying drawings in which:

FIG. 1 is a side elevational view of one form of syringe made in accordance with the present invention;

FIG. 2 is an enlarged cross-sectional view taken substantially along the line 2—2 of FIG. 1;

FIG. 3 is an enlarged cross-sectional view taken substantially along the line 3—3 in FIG. 1;

FIG. 4 is an enlarged cross-sectional view taken substantially along the line 4—4 of FIG. 1;

FIG. 5 is a view similar to FIG. 4 showing a modified construction of the syringe.

FIG. 6 is an enlarged, exploded perspective view illustrating a locking means for a valve to be used in conjunction with the present invention; and, FIG. 7 is a perspective view showing a modified form of the present invention.

Referring now more particularly to the drawings, and to those embodiments of the invention here shown by way of illustration, FIG. 1 shows an expandable syringe 10 having an expandable bag 10a with a filling means 11 at one end thereof, and a dispensing means 12 at the opposite end thereof. Filling means 11 is shown in this embodiment as a filling receptacle having a one-way valve therein which will permit the introduction of a liquid such as water into the syringe and create a presurized condition therein.

Filling means 11 is shown in greater detail in FIG. 3 and reference is now made to that Figure. The filling means 11 includes a substantially cylindrical body 18 having a hemispherical end 19 integrally joined to the bag 10a. The distal end of body 18 is provided with a diaphragm 20 having a central opening 21 therein. It will be understood that the entire filling means 11 is made of a rubber or other suitable elastic material so that the diaphragm 20 may be urged over the spout of a water faucet with the spout projecting through the opening 21. Since the diaphragm is elastic the opening 21 of the diaphragm will seal around the spout of the water faucet so that water from the spout is introduced into the body 18.

It is recognized that numerous water faucets are now equipped with aerators which include openings in the sides of the spout of the water faucet. As shown in FIG. 3 of the drawings, member 11 is formed so that a spout S of a water faucet may be received within the body 18 sufficiently so that the aeration openings 13 are fully received within the body 18 and beyond opening 21 of the diaphragm. With this arrangement water from the aeration openings of the aerated spout will be contained within the body 18.

Body 18 contains a one-way valve 22 spaced from diaphragm 20 a distance sufficient to permit the insertion of a spout S. One-way valve 22 consists of a web 22a having a central opening 24 and a flap valve 25 resiliently overlying and closing opening 24. Flap valve 25 is formed integrally at one end with web 22 and the flap valve 25 is separated from web 22a along the line 26. As liquid is emitted from spout S under pressure, the disconnected end of the flap valve is moved away from web 22a, as shown by the broken line representation, to allow the liquid to pass through the opening 24 past the web 22a and into the bag 10a.

As liquid is admitted through the opening 21, and into the bag 10a and accumulates therein to expand the bag 10a, the liquid within the bag 10a will be under increasing pressure from the tension of the bag 10a. When the pressure within the bag 10a equals the line pressure of the liquid from the faucet, the flap valve 25 will close. At this point the spout may be removed from the opening 21 in the diaphragm and the flap valve 25 will remain closed as a result of pressure from the presurized liquid within the bag 10a and the liquid will be contained within the syringe 10.

Attention is now directed to FIG. 2 of the drawings wherein dispensing means 12 is disclosed in position in the opposite end of bag 10a. It should be noted that bag 10a includes an open end 30 having a substantially cylindrical body 32 with a hemispherical end 31 integrally joined to bag 10a. Cylindrical body 32 terminates at the open end of the bag 10a in a circumferential bead 34. A threaded mouthpiece 35 is fitted within the body 32 and expands the body 32 outwardly to distort its normally cylindrical configuration.

Mouthpiece 35 is formed from a substantially rigid plastic material that is easily molded, light in weight, and suitable for sanitizing and use in association with chemicals that are normally used in such a syringe. The mouthpiece 35 includes a tubular base section 36 that is received within the body 32 of the bag. The base section 36 terminates in an annular shoulder 38 and a tubular mouth section 39, having external threads 40 formed thereon, projects from the shoulder. At the point of junction between the tubular mouth section 39 and the shoulder 38, there is formed an annular groove 37.

The mouthpiece 35 is formed with an enlarged base section 36 for receipt within the body 32, and for expanding the body 32 outwardly to assure a tight fit of the body 32 against the base 36. The bead 34 of the body 32 is urged inwardly by its natural elasticity to be received within the peripheral groove 37 and to engage the shoulder 38. Threaded mouth section 39 extends outwardly beyond the bead 34 for receipt of cap 14 which engages threads 40.

Cap 14 includes a cylindrical body 41 having internal threads 42, complementary to the threads 40 on mouth 39. Cap 14 further includes a top section 44 having a central tubular valve portion 48 positioned thereon. Valve section 48 defines a discharge port 46 which is in communication with the interior of cap 14 through opening 45 on the top section 44.

Cap 14 also includes an off-set skirt 43 extending from cylindrical body 41. Skirt 43 is formed integrally with the body 41 and is of a slightly larger diameter. When cap 14 is threaded onto the mouthpiece 39 and rotated so that a portion of the complementary threads 40 and 42 engage, skirt 43 surrounds a portion of the base section 36 with the elastic body 32 therebetween. As the cap 14 is rotated, cylindrical body 41 engages the bead 34 and compresses the bead against the shoulder 38 to effect a seal between the bag 10a and the mouthpiece 35. Skirt 43 prevents outward movement of the bead 34 and the body 32 to prohibit inadvertent separation of the body 32 from the mouthpiece 35. It will be noted that cap 14 includes ridges on its external surface, and the body 32 is knurled, to assist a person in gripping and rotating the cap with respect to bag 10a.

Tubular valve portion 48 cooperates with a nozzle section 49 to form valve 16. When the nozzle section 49 is moved axially away from the cap 14, valve 16 is opened so that liquid may pass from the syringe bag 10a through the tubular valve section 48 and into passage 50 of the nozzle. When the nozzle section 49 is urged axially towards the cap 14, the valve 16 is closed so that liquid cannot pass therethrough.

The present syringe may be filled with liquid by placing the filling means 11 over the spout of a water faucet or the like so that liquid is forced through the flap valve 25 and into the bag 10a. When the bag 10a is stretched to proper capacity by the line pressure of the faucet, flap valve 25 will close to retain the liquid therein. During introduction of liquid into bag 10a, cap 14 is in place and the valve 16 is closed so that the bag 10a will fill with liquid.

During use, the valve 16 is opened by urging nozzle section 49 axially away from cap 14 to release the contents of bag 10a. Bag 10a may be squeezed if desired to pump the liquid therein out through the nozzle section.

Following use of the syringe, cap 14 may be removed from mouth section 39 thereby providing a large opening into bag 10a for a thorough rinsing and emptying of the bag. Referring to FIG. 4 of the drawings, it will be seen that the bag 10a is substantially flat so that, when emptying the bag 10a, one might find it convenient to twist the bag to exert compressive pressure between the two opposed walls 51 and 52 of the bag and squeeze additional liquid from the bag.

Referring to FIG. 5 of the drawings, it will be seen that an alternative embodiment for the bag 10a is shown. The bag 10a of this embodiment has an upper wall 54 and a lower wall 55 joined by V-shaped sidewalls 56 and 58. The construction shown in FIG. 5 will be most desirable for a syringe 10 of greater capacity since the V-shaped walls 56 and 58 can straighten allowing the opposed walls 54 and 55 to move further away from each other for receiving a greater quantity of liquid.

In some instances, and especially when the device is to be used as a syringe for an enema, there is a possibility that the valve 16 may close inadvertently. The valve shown in FIG. 6 is therefore provided to solve this problem. This modified valve, designated as 16a, is substantially identical to the valve 16 with the exception that valve 16a includes means for locking the valve in an open and a closed position.

As shown in FIG. 6, the valve section 60 is similar to the nozzle section 49 in FIG. 2 and the valve section 62 is similar to the tubular valve portion 48 of FIG. 2. The difference between the valve 16 and the valve 16a comprises the addition of a locking lug 64 on the valve section 62, which is parallel to the axis of valve section 62. Ring 61 on the interior surface of valve section 60 is discontinuous and defines a slot 68 to cooperate with lug 64.

When valve 16a is assembled, ring 61 is snapped over the head 66 of section 62. Ring 61 rides along neck 69 of section 62 for the valve to be opened and closed while lug 64 is aligned with slot 68 in the ring. When lug 64 is misaligned with respect to slot 68 by rotation of valve section 60 with respect to valve section 62, valve section 60 can not be moved axially with respect to valve section 62. Misalignment of lug 64 may be accomplished while the valve 16 is either in an open or closed relationship so that the valve 16 may be locked into that condition until the lug 64 is aligned with slot 68 in ring 61.

FIG. 7 of the drawings shows a further modification of the present invention. It should be understood that in a hospital environment, it may be desirable to suspend the syringe 10 at a remote location and employ a section of tubing to transfer liquid from the syringe to a patient. Under those circumstances, the filling means end of the syringe is provided with a strap 72 for suspending the syringe from a stand or other suitable support.

With the syringe suspended from a support, a length of tubing 75 is used to administer liquid to a patient. The nozzle section 12 as shown in FIGS. 1 and 2 is replaced with a hose connector section 74 which provides the valve capabilities of nozzle section 12. The hose connector 74 includes the elements of nozzle section 12 as shown in FIG. 2, so that a valve, such as valve 16 or 16a is still employed.

The hose connector 74 is adapted to receive one end of hose 75, the opposite end of which carries a conventional nozzle 76. The nozzle 76 may be adapted for a douche, an enema, or other conventional uses well known to those skilled in the art.

It will of course, be understood that other and further changes and modifications may be made, and the full use of equivalents resorted to, without departing from the spirit or scope of the invention as defined by the appended claims.

What is claimed is:

1. An expandable syringe, of the type including an elastic bag stretchable on filling with liquid under pressure, said syringe including a filling means at one end of said elastic bag, said filling means including means for receiving a spout through which said liquid under pressure is admitted to said bag and a filling valve between said means for receiving a spout and said elastic bag, said syringe including a dispensing means at the opposite end of said elastic bag, said dispensing means comprising a mouthpiece receivable in an opening in said opposite end of said elastic bag, a cap threadedly engageable with said mouthpiece and having a discharge port therein, a valve part carried by said cap in communication with said discharge port, said valve part being adapted to receive a second valve part to open and close said discharge port.

2. An expandable syringe as claimed in claim 1, said mouthpiece including a base portion receivable within said opposite end of said elastic bag, a mouth portion extending from said opposite end of said elastic bag, a bead on said elastic bag surrounding said opening in said opposite end, and means carried by said cap for retaining said bead against said mouthpiece.

3. An expandable syringe as claimed in claim 2, said mouthpiece having a shoulder between said base portion and said mouth portion, and defining a groove for receiving said bead, said means carried by said cap for retaining said bead comprising a skirt, said skirt being so constructed and arranged as to overlie said opposite end of said elastic bag and to prevent outward movement of said bead.

4. An expandable syringe as claimed in claim 3, said second valve part including a nozzle formed integrally therewith, said first valve part and second valve part being so constructed and arranged that motion of said second valve part with respect to said first valve part opens said discharge port and provides communication between said elastic bag and said nozzle.

5. An expandable syringe as claimed in claim 3, said second valve part including means for receiving a tubing thereover, said first valve part and said second valve part being so constructed and arranged that motion of said second valve part with respect to said first valve part opens said discharge port and provides communication between said elastic bag and said tubing.

* * * * *